(12) United States Patent
Varlet et al.

(10) Patent No.: US 11,793,475 B2
(45) Date of Patent: Oct. 24, 2023

(54) METHOD AND SYSTEM FOR OBTAINING OPERATING PARAMETERS FOR 3D X RAY ACQUISITION

(71) Applicant: TROPHY, Croissy-Beaubourg (FR)

(72) Inventors: Stephane Varlet, Chenehutte (FR); Olivier Nesme, Nogent-sur-Marne (FR); Laurent Boutte, Ozoir-la-Ferriere (FR); Stephane Alric, Paris (FR); Aude Lagardere, Paris (FR)

( * ) Notice: Subject to any disclaimer, the term of this patent is extended or adjusted under 35 U.S.C. 154(b) by 0 days.

(21) Appl. No.: 17/592,756

(22) Filed: Feb. 4, 2022

(65) Prior Publication Data

US 2022/0361829 A1 Nov. 17, 2022

Related U.S. Application Data

(63) Continuation of application No. 16/652,031, filed as application No. PCT/EP2018/076172 on Sep. 26, 2018, now abandoned.

(30) Foreign Application Priority Data

Sep. 29, 2017 (EP) ..................................... 17306306

(51) Int. Cl.
*A61B 6/03* (2006.01)
*A61B 6/06* (2006.01)
(Continued)

(52) U.S. Cl.
CPC ................ *A61B 6/14* (2013.01); *A61B 6/032* (2013.01); *A61B 6/04* (2013.01); *A61B 6/06* (2013.01);
(Continued)

(58) Field of Classification Search
CPC .. A61B 6/14; A61B 6/032; A61B 6/04; A61B 6/06; A61B 6/4085; A61B 6/469;
(Continued)

(56) References Cited

U.S. PATENT DOCUMENTS

2015/0190102 A1* 7/2015 Bruno .................... A61B 6/542
378/39

\* cited by examiner

*Primary Examiner* — Courtney D Thomas

(57) ABSTRACT

The invention concerns a method for obtaining operating parameters for an x-ray CBCT imaging apparatus in view of acquiring a set of data of a patient's maxillofacial region. The method comprises: identifying a patient's maxillofacial first region of interest (ROI1), determining a height of a horizontal plane of said patient's maxillofacial first region of interest (ROI1) when the patient is in an occlusion position or bites a patient positioning accessory, acquiring through a slit-shaped collimator window a first set of data relative to said patient's maxillofacial first region of interest (ROI1) including the horizontal plane using x-ray CBCT imaging, reconstructing an axial CBCT slice comprising the horizontal plane based on the first set of data relative to the patient's maxillofacial first region of interest (ROI1), displaying the reconstructed axial CBCT slice of the patients maxillofacial first region of interest (ROI1) from the acquired first set of data, defining at least partially a second region of interest (ROI2) based on the displayed reconstructed axial CBCT slice of the patient's maxillofacial first region of interest (ROI1) and intersecting the latter, obtaining operating parameters for an x-ray CBCT imaging apparatus based on at least the defined second region of interest (ROI2) in view of acquiring a second set of data including the defined second region of interest (ROI2).

18 Claims, 4 Drawing Sheets

(51) Int. Cl.
*A61B 6/00* (2006.01)
*A61B 6/14* (2006.01)
*A61B 6/04* (2006.01)

(52) U.S. Cl.
CPC ............ *A61B 6/4085* (2013.01); *A61B 6/469* (2013.01); *A61B 6/485* (2013.01); *A61B 6/488* (2013.01); *A61B 6/5217* (2013.01)

(58) Field of Classification Search
CPC ....... A61B 6/485; A61B 6/488; A61B 6/5217; A61B 6/542; A61B 6/0421; A61B 6/465; A61B 6/544; A61B 6/545; G16H 50/30
See application file for complete search history.

METHOD AND SYSTEM FOR OBTAINING OPERATING PARAMETERS FOR 3D X RAY ACQUISITION

TECHNICAL FIELD

The disclosure relates generally to the field of dental x-ray imaging and in particular to the field of x-ray CBCT (Cone Beam Computed Tomography) imaging. More specifically, the disclosure relates to a method for obtaining operating parameters for an x-ray CBCT imaging apparatus and a system for obtaining operating parameters for x-ray CBCT imaging a patient's maxillofacial region.

BACKGROUND

Conventional methods and systems for obtaining a radiographic image of a patient's maxillofacial region through x-ray CBCT imaging very often require irradiating local areas of reduced size relative to the size of the whole patient's maxillofacial region with an x-ray dose during a certain exposure time in order to obtain details on teeth, specific areas, etc. that are of interest to the practitioner.

Predefined apparatus settings corresponding to an average patient allow to reach the desired local areas.

However, image retaking may occur due to variation between patients regarding the average predefined settings, thereby leading to an increase in the x-ray dose received by the patient.

While such systems may have achieved certain degrees of success in their particular applications, there is nevertheless a need to improve these methods and systems.

SUMMARY

An object of the present disclosure is to avoid unnecessary x-ray doses for the patients when undergoing an x-ray CBCT examination.

Another object of the present disclosure is to improve the positioning accuracy of a patient's data volume acquired through an x-ray CBCT data acquisition while limiting the patient dose exposure.

Still another object of the present disclosure is to optimize the adjustment of operating or acquisition parameters of an x-ray CBCT imaging apparatus before submitting a patient to an x-ray CBCT examination.

These objects are given only by way of illustrative example, and such objects may be exemplary of one or more embodiments of the invention. Other desirable objectives and advantages inherently achieved by the invention may occur or become apparent to those skilled in the art. The invention is defined by the appended claims.

According to one aspect of the disclosure, there is provided a method for obtaining operating parameters for an x-ray CBCT imaging apparatus in view of acquiring a set of data of a patient's maxillofacial region, the method comprising:

identifying a patient's maxillofacial first region of interest ROI1, determining a height of an horizontal plane of said patient's maxillofacial first region of interest ROI1 when the patient is in an occlusion position or bites a patient positioning accessory, acquiring through a slit-shaped collimator window a first set of data relative to said patient's maxillofacial first region of interest ROI1 including the horizontal plane using x-ray CBCT imaging, reconstructing an axial CBCT slice comprising the horizontal plane based on the first set of data relative to the patient's maxillofacial first region of interest ROI1, displaying the reconstructed axial CBCT slice of the patient's maxillofacial first region of interest ROI1 from the acquired first set of data, defining at least partially a second region of interest ROI2 based on the displayed reconstructed axial CBCT slice of the patient's maxillofacial first region of interest ROI1 and intersecting the latter, obtaining operating parameters for an x-ray CBCT imaging apparatus based on at least the defined second region of interest ROI2 in view of acquiring a second set of data including the defined second region of interest ROI2.

The method according to an embodiment of the invention is a novel method which makes it possible to reduce the patient exposure to x-rays.

The method according to an embodiment of the invention is a novel method which uses a first x-ray "pre-shoot" with an x-ray dose to obtain and reconstruct a CBCT slice comprising the patient's maxillofacial first region of interest ROI1 and that enables selection or definition of a more specific area or region of interest by the practitioner. This definition or selection of a more specific area or region of interest makes it possible to obtain adapted operating or acquisition parameters that will be used for another "shoot" or second x-ray CBCT data acquisition.

Typically a low dose is used for the "pre-shoot". A low is a dose that does not exceed 20%, preferably less than 10% and more preferably less than 5% of the default or standard dose (obtained with default or standard parameters) that is used for a known x-ray examination (3D, panoramic etc.). A low dose may be used since the CBCT slice does not need many details as in a default or conventional acquisition and the patient must not be too much exposed to x-rays. However, the CBCT slice information has to be sufficient to provide morphology information (ex: location of teeth, geometry of teeth, etc.) enabling selection of a more specific area or region of interest by the practitioner. The information that is contained in the CBCT slice is proper to the patient. Use of such information therefore enables more adapted and/or accurate definition of a more specific area or region of interest. This way of proceeding is clearly not based on averaged patient's data as in the past. The operating or acquisition parameters that are obtained based on such a more specific area or region of interest of the patient will thus be more reliable and accurate since they will be representative of the patient. The CBCT slice may be a thin slice that includes the ROI1. The slice may be less than 100 μm thick or high or a slice integrated over a certain thickness or height typically in the order of a few mms.

The patient is preferably in a repeatable position during the "pre-shoot", thereby meaning that for a subsequent "shoot" or acquisition with the obtained parameters the patient will be in the same or in a very close position. In this respect, the setting parameters of the x-ray apparatus for positioning the patient are kept in memory.

According to possible features or aspects:

defining at least partially the second region of interest ROI2 based on the displayed reconstructed axial CBCT slice of the patient's maxillofacial first region of interest ROI1 includes defining the position of the second region of interest ROI2 in the x, y plane of the axial slice;

defining the second region of interest ROI2 further includes defining the position of the second region of interest ROI2 along a z axis (height) that is perpendicular to the x, y plane of the axial slice;

defining the z-axis position of the second region of interest ROI2 includes beforehand one of the following:

acquiring a lateral x-ray scout view comprising the patient's maxillofacial first region of interest ROI1; the scout view may be used to position both the height of the horizontal plane of ROI1 and the height and the size in the y, z plane of ROI2; acquiring an optical image comprising the patient's maxillofacial first region of interest ROI1 including landmarks;

performing physical measurements on the patient's maxillofacial first region of interest ROI1 using a patient positioning device;

the method further comprises adjusting the height of the second region of interest ROI2 based on the lateral scout view, the optical image or the performed physical measurements;

the z-axis position of the second region of interest ROI2 is predetermined;

the second region of interest ROI2 has a size that is selected among a set of predetermined values;

defining the z-axis position of the second region of interest ROI2 is based on determining the height of an horizontal plane of said patient's maxillofacial first region of interest ROI1 when the patient is in an occlusion position or bites a patient positioning accessory;

determining a height of an horizontal plane of said patient's maxillofacial first region of interest ROI1 when the patient is in an occlusion position or bites a patient positioning accessory includes beforehand one of the following:

acquiring a lateral x-ray scout view comprising the patient's maxillofacial first region of interest ROI1;

acquiring an optical image comprising the patient's maxillofacial first region of interest ROI1 including landmarks;

performing physical measurements on the patient's maxillofacial first region of interest ROI1 using a patient positioning device;

the first set of data is acquired while the patient is maintained in a first position through a patient positioning device, said first patient position being defined by a set of setting parameters for the patient positioning device;

the method comprises prior adjusting the setting parameters of the patient positioning device before acquiring the second set of data;

the first set of data and the second set of data are separate in time;

the x-ray CBCT imaging apparatus comprises an x-ray source and an x-ray sensor that are both operable to simultaneously move around the patient's head along a predetermined trajectory and obtaining operating parameters for the x-ray CBCT imaging apparatus based on the defined second region of interest ROI2 comprises adjusting a trajectory for both x-ray source and x-ray sensor based on the defined second region of interest ROI2.

According to another aspect of the disclosure, there is provided a system for obtaining operating parameters for x-ray CBCT imaging a patient's maxillofacial region, comprising:

an x-ray source and at least one x-ray sensor that are configured to move around a patient's maxillofacial first region of interest ROI1 while irradiating the latter with a slit-shaped x-ray beam so as to acquire a first set of data relative to said patient's maxillofacial first region of interest ROI1 when the patient is in an occlusion position or bites a patient positioning accessory, said patient's maxillofacial first region of interest ROI1 including an horizontal plane of the patient in an occlusion position or a plane parallel thereto, a microprocessor configured to:

reconstruct an axial CBCT slice comprising the occlusal plane or the plane parallel thereto based on the first set of data relative to the patient's maxillofacial first region of interest ROI1, display the reconstructed axial CBCT slice of the patient's maxillofacial first region of interest ROI1 from the acquired first set of data with a view to defining at least partially a second region of interest ROI2 that is based on the displayed reconstructed axial CBCT slice and intersects the latter, obtain operating parameters for an x-ray CBCT imaging apparatus based on at least the defined second region of interest ROI2 in view of acquiring a second set of data including the defined second region of interest ROI2.

The microprocessor may also be configured to perform any of the steps, operations, features or aspects of the above method.

According to still another aspect of the disclosure, there is provided a computer storage medium having instructions stored therein for causing a computer or a microprocessor to perform the method as briefly mentioned above.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE EMBODIMENTS

Figure 1:
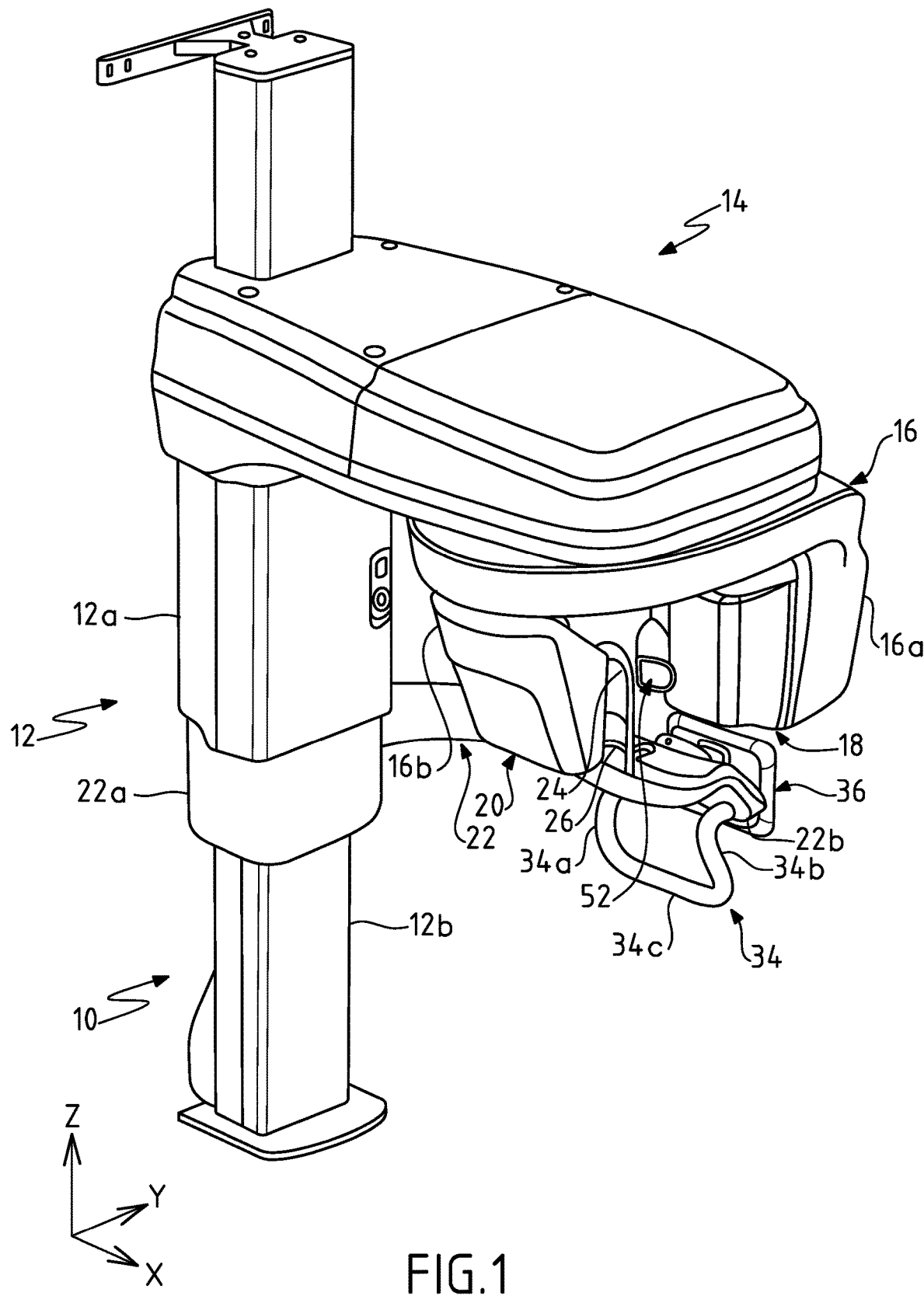
FIG. 1 shows an overall schematic perspective view of an x-ray CBCT imaging apparatus according to an embodiment of the invention.

The following is a detailed description of the preferred embodiments, reference being made to the drawings in which the same reference numerals identify the same elements of structure in each of the several figures.

FIG. 1 illustrates an embodiment of an x-ray imaging apparatus, in particular an extra-oral imaging apparatus 10. Apparatus 10 comprises a support structure that includes a support frame 12 which may be a support column.

The support structure also includes a horizontal mount 14 that may be supported or held by the vertical column 12. Horizontal mount 14 extends away from vertical column 12 and may be substantially perpendicular thereto. Horizontal mount 14 can move vertically relative to the vertical column 12.

More particularly, horizontal mount 14 is fixedly mounted on a vertical part 12a that is slidably mounted over a fixed vertical part 12b. For example, an actuator, e.g. of the electric type, located behind the vertical column (not represented in the drawing) can be commanded to drive the horizontal mount 14 into a vertical movement in a controlled manner.

Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation which may be stationary during the operation of the imaging process or may follow one among several predetermined trajectories in accordance with the selected imaging process. A driving known mechanism (not represented in the drawing) for driving the gantry 16 into a given movement is integrated inside horizontal mount 14. By way of example, such driving mechanism includes motors for imparting a first movement in an x, y plane, e.g. two step-by-step motors, and a motor for imparting a rotational movement about the vertical axis z, e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto.

X-ray source 18 includes a conventional collimator (not represented in FIG. 1). The position of the collimator along the vertical axis z and the opening of the slit collimator window may be adjusted so that the collimated x-ray beam irradiates a region of interest of the patient's head or patient's maxillofacial region.

When activated x-ray source 18 emits an x-ray beam which here irradiates an imaging area of a patient's maxillofacial region (or patient's maxillofacial region of interest) before impinging the at least one x-ray sensor 20.

In the present embodiment, x-ray source 18 and the at least one x-ray sensor 20 are configured to move around the patient's maxillofacial region along a predetermined trajectory, while irradiating the imaging area of the patient's maxillofacial region.

In the present embodiment, the apparatus 10 is used in an x-ray CBCT operating mode and here, more particularly, in a CBCT operating mode for obtaining a 3D CBCT slice as will be seen subsequently. The apparatus 10 may be considered as an x-ray CBCT imaging apparatus to perform volumetric or computerized tomography and obtain 3D images.

However, the apparatus 10 may also function according to one or several other operating modes or imaging processes, such as panoramic, cephalometric, etc.

The apparatus 10 is also able to operate according to such different operating modes or only some of them.

In this respect, another sensor or other sensors may be used and the x-ray may be collimated accordingly to irradiate a region of the patient's head as the patient's maxillofacial region of interest (or the whole patient's head) with a specific shape depending on the selected operating mode and choice of the practitioner.

The at least one x-ray sensor 20 includes a sensor that is adapted to one of the operating modes of the apparatus. For instance, the sensor may be adapted to perform a CBCT scan, e.g. a volumetric or computerized sensor (e.g. rectangular, square-shaped), or several sensors of the previous type.

The support structure may also include a patient positioning accessory support member 22 which here is an arm. Arm 22 is connected to the support frame, and more particularly to the vertical column 12. The patient positioning arm 22 is movable relative to the support frame. More particularly, arm 22 can slide along the vertical column 12 so as to move up or down upon command through appropriate actuator(s) e.g. of the electric type. The patient positioning arm 22 extends from an arm support 22a that is slidably mounted relative to the fixed vertical part 12b. The patient positioning arm 22 extends along the apparatus in a direction that is substantially in correspondence with the direction of extension of horizontal mount 14. Patient positioning arm 22 is here arranged sideways relative to the apparatus in a substantial parallel relationship with horizontal mount 14.

Patient positioning arm 22 serves to position the patient in the apparatus at a given location.

Patient positioning arm 22 may include one of several patient positioning accessories generally located at a free end 22b of the arm or proximate thereto. These accessories may also or alternatively be considered as holding systems.

These patient positioning accessories allow to position the anatomical structures of the patient's head according to different orientations and to immobilize the patient's head during the examination so as to reduce any possible movement.

There exists one or several types of patient positioning accessories for each type of specific examination to be carried out by the apparatus according to different operating modes. The arm 22 is configured to accommodate each of these patient positioning accessories of different types, generally one at a time.

As illustrated in FIG. 1, one of these patient positioning accessories, noted 24, includes two temporal holding members that extend upwardly from the arm 22 to which they are removably attached. Only one temporal holding member is represented, the other one being hidden by the arm 16b.

The patient positioning accessory 24 may also include a chin rest 26 that extends upwardly from the arm 22 to which it is removably attached. The chin rest 26 is located between the two temporal holding members to position a patient's head for a panoramic examination. A standard bite block may be further added to the chin rest.

Alternatively, a Frankfort guide bite block may be used for panoramic examination.

Other possible types of patient positioning accessories may be envisaged: a nasal support for conducting a temporal mandible joint examination with open and closed mouth, a bitten support for 3D examination (bit type), a frontal support for 3D examination (frontal type), a combination of a bite support and a frontal support, etc.

In addition, a seat (not represented in the drawing) may be used for the patient according to the type of examination. This arrangement may help to set the position of the patient and also the repeatability of this position in the future, for subsequent data acquisition. Even though subsequent data acquisition is not performed on the same apparatus, the setting parameters defining the patient's position (including the position relative to the seat) may be stored in memory.

As illustrated in FIG. 1, a handle assembly 34 may be positioned at the free end 22b of the arm, underneath the arm and in a parallel relationship with the arm. This handle assembly 34 includes two vertical separate handle portions 34a, 34b which can be grasped by the patient when undergoing an imaging process so as to remain motionless.

Overall this handle assembly 34 has a U-shape which includes a horizontal base portion 34c and two vertical upwardly-extending branches 34a, 34b that are fixed to the arm 22. Each branch plays the role of a vertical handle portion.

Other handle assemblies may alternatively be used for handling the arm 22.

Patient positioning arm 22 may also support a monitor or display assembly 36 which makes it possible for a practitioner of the apparatus to view images displayed thereon, interact therewith and drive certain functions of the apparatus.

Figure 2:
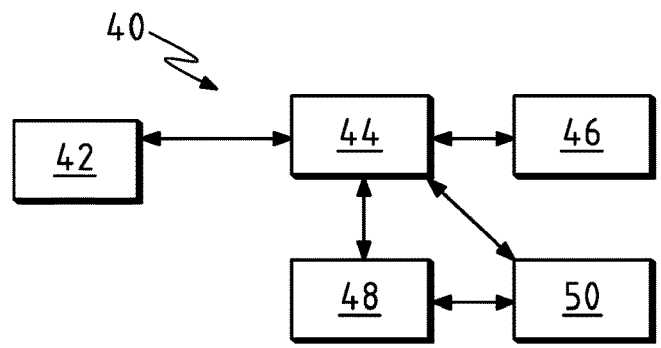
FIG. 2 shows main functional components or assemblies of an x-ray CBCT imaging system according to an embodiment of the invention.

FIG. 2 is a schematic view of main functional components or assemblies of a system for obtaining operating parameters 40 that will be used in the present embodiment.

Some or all of these components or assemblies may be part of the apparatus 10 or not. In the present embodiment system 40 is located in the apparatus 10.

System 40 comprises an acquisition assembly 42 that includes the x-ray source and x-ray sensor of FIG. 1 apparatus.

System 40 comprises a control assembly 44 that is connected to acquisition assembly 42 and configured to control operation of the latter according to embodiment methods of the invention.

Control assembly 44 may also be used to enable operation of the apparatus 10 and its different components/assemblies in a more conventional manner, in particular to perform CBCT scans and reconstruct 3D volumes (3D x-ray image data) and perform panoramic, cephalometric, etc. data acquisition.

Control assembly 44 includes in particular a microprocessor and possibly one or more storage medium for storing a computer program having instructions for controlling system 40 to practice one or several embodiment methods according to the present invention. When the microprocessor executes the computer program stored in the one or more storage medium the microprocessor is considered as being configured to perform steps or operations of the embodiment method according to the present invention.

An aspect of the present invention is also directed to a computer program product including the one or more storage medium.

The above one or more storage medium may be, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store such a computer program.

The stored computer program(s) or other stored computer program(s) may have also instructions for controlling the apparatus 10 to practice more conventional methods such as conventional methods for obtaining a 3D volume.

System 40 may also comprise one or more external storage medium 46 that store, here, different volumes of data reconstructed by the apparatus in the course of x-ray imaging processes, e.g. CBCT imaging processes. The one or more external storage medium 46 may also be of the same type as described above.

The one or more external storage medium 46 may also store the above computer program(s) for controlling system 40 and/or, more generally, for controlling the apparatus 10 instead of the one or more storage medium inherent to control assembly 44.

System 40 further comprises a display assembly 48, here a monitor or screen or several of them, that may correspond to display assembly 36 of FIG. 1. Display assembly 48 is connected to control assembly 44.

Display assembly 48 may display, automatically or on demand, selected images of a patient's maxillofacial region obtained from an x-ray CBCT imaging process performed by the apparatus 10.

Display assembly operates under control of control assembly 44.

System 40 may further comprise a user interface assembly 50 that is connected to display assembly 48 and control assembly 44. User interface assembly 50 allows a user, e.g. a practitioner or technician, to interact with the display assembly 48, and possibly control assembly 44 that executes image processing/algorithms, in order to perform different tasks.

The user interface assembly 50 may include one or more interaction devices connected to display assembly 48, such as, but not limited to, a pointing device, e.g. a computer mouse joystick, a stylet, a keypad, a touchpad etc.

Other types of interaction devices or tools (user interface tools) may alternatively, or in addition, be used: a touch screen, tool icons displayed or that may be displayed on command on the screen, etc.

Assemblies 44, 46, 48 and 50 may be located in whole or in part in the arm 22 of apparatus 10 or remotely-located relative to the apparatus (e.g. in the same room or in a separate room or in another place). If control assembly 44 is not located in the apparatus 10, another control assembly may be present in the apparatus so as to control the acquisition assembly 42 and, in a general manner, the operation of the apparatus. However, the whole description applies equally whatever the location of the assemblies.

The above also applies if assemblies 42, 44, 46, 48 and 50 pertain to another x-ray imaging apparatus.

An embodiment method according to the invention will now be described with reference to FIG. 3 which depicts an algorithm of the corresponding computer program(s). This algorithm makes reference to other algorithms that are illustrated on other figures and that may be part of the same computer program or correspond to other computer programs.

For its operation the embodiment method makes use of functional components or assemblies that can be those described above in connection with FIG. 1 apparatus 10 and FIG. 2. Alternatively, the functional components or assemblies necessary to perform the method may be those of another x-ray imaging apparatus although they may be in accordance with the configuration of FIG. 2 (all the components of FIG. 2 may not be present).

A patient is first positioned in the working space of apparatus 10 between the x-ray source 18 and x-ray sensor 20 of acquisition assembly 42, e.g. in a sitting position. The method starts with an identification step S1 for identifying a patient's maxillofacial first region of interest denoted ROI1. The practitioner identifies ROI1 based on predetermined criteria such as the type of examination to be carried out on a second region of interest ROI2 of the patient's maxillofacial region, the second region of interest ROI2 itself, etc.

For example, ROI1 may include the upper and lower jaws, part of both jaws, only one jaw, part of a single jaw etc. depending on the interest of the practitioner.

The method further comprises a height determination step S2. For the performance of this step the patient may bite in a patient positioning member or accessory and his/her teeth are then spaced from a few millimeters. Such a patient positioning member or accessory may be attached to the arm 22 in a releasable manner. Such a patient positioning member or accessory may be a bite block, e.g. a Frankfurt guide bite block used for panoramic examination, a standard bite block, a bitten 3D support etc.

Figure 5:
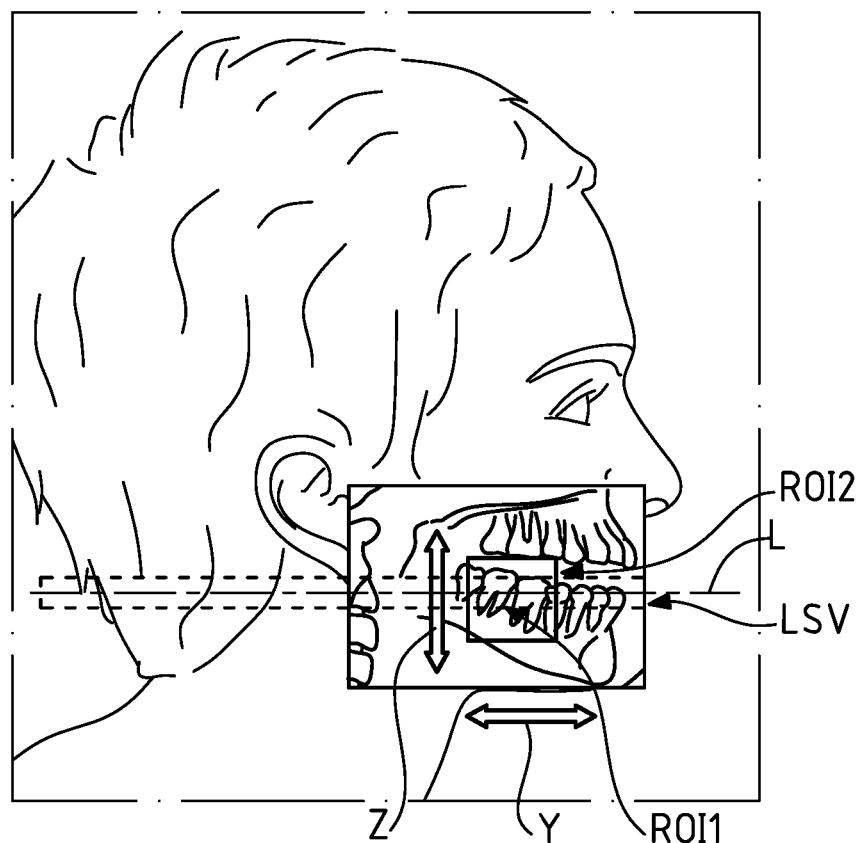
FIG. 5 shows the possible positions of the ROI1 and ROI2 in a y, z plane with a lateral scout view.

FIG. 5 illustrates ROI1 that has been identified/selected by the practitioner on a previously acquired lateral scout view LSV of the patient's maxillofacial region (mere projection of data acquired through a lateral x-ray data acquisition). On FIG. 5 the patient's face is also illustrated as a background. The resulting view may be displayed on display assembly 48.

On FIG. 5 the biting block has not been represented for the sake of clarity.

Alternatively, the patient may be in an occlusion position, i.e. his/her upper and lower jaws have to be in contact with each other. His/her head may be maintained in position through a chin rest, a frontal support including a chin rest etc. The identified ROI1 may include the occlusal plane in this alternative arrangement.

The aim of this step is to determine a height of a horizontal plane within ROI1. This height will be used next for a first x-ray data acquisition to be described later on.

This horizontal plane may be a median plane of ROI1 or another plane within ROI1.

For the performance of this step the patient may also be positioned so that his/her Camper plane be horizontal.

Figure 4:
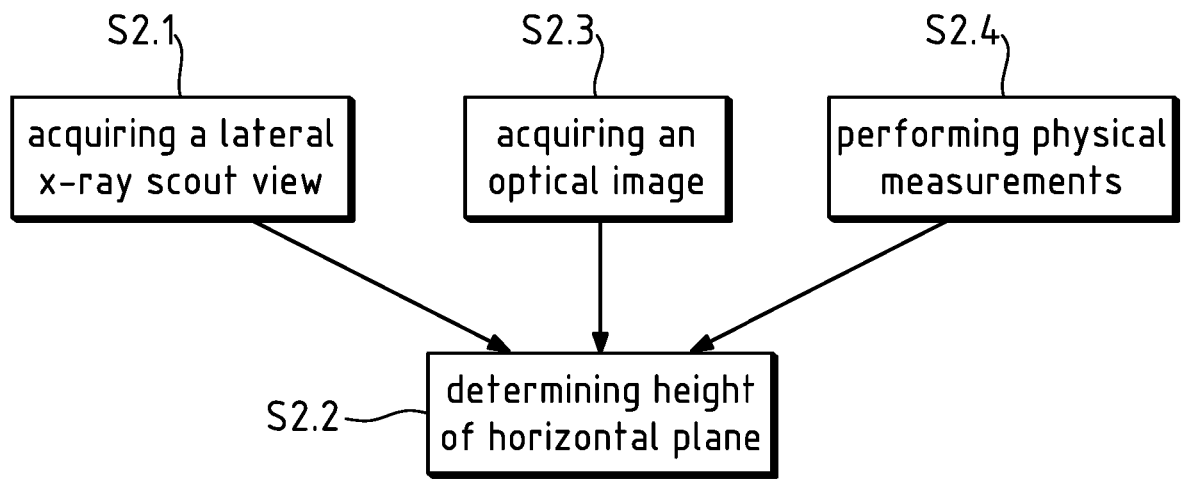
FIG. 4 shows different processes to perform the FIG. 3 step S1.

FIG. 4 shows different ways for determining the height of the horizontal plane.

A first way is to acquire an x-ray lateral scout view of the patient (step S2.1) through the acquisition assembly 42 operated under the control of control assembly 44 of FIG. 2. The position of the scout view relative to the patient's jaw may have been previously determined based on predetermined mean values.

FIG. 5 that has been already mentioned above schematically illustrates an x-ray lateral scout view of the patient that has been acquired in a conventional manner. Such a view provides here information on the location of the upper and lower jaws and shows the above-discussed patient's maxillofacial first region of interest ROI1 that has been identified by a practitioner. ROI1 includes here the upper part of the lower jaw of the patient and extends to the back of the patient's head. However, the extension of ROI1 may be shorter along y axis. Alternatively, ROI1 may have been positioned differently by the practitioner relative to the jaws and its extension may be or not shorter along y axis.

An horizontal plane of interest of ROI1 may be positioned on display by the practitioner or determined by computation. The horizontal plane may be the median plane of ROI1 as already mentioned above.

Next, at step S2.2 the height of this horizontal plane is determined in a conventional manner based on the known position of the scout view relative to the used patient's positioning accessory (here a bite block) and the known position of the latter relative to the x-ray apparatus, in particular the arm 22 or any other reference part of the apparatus. To be noted that the position of the x-ray source relative to the arm is also known.

FIG. 5 illustrates the z axis position of the above-mentioned horizontal plane by the line denoted L.

Two other ways for determining the height of a horizontal plane are illustrated on FIG. 4.

A second way (step S2.3) makes provision for acquiring at least one optical image of the patient (in a biting position or in the occlusal position) comprising the patient's maxillofacial first region of interest ROI1 including landmarks. The at least one image is more particularly a facial image taken by a camera and the landmarks may be of the anatomical type (ex: the corners of the mouth or landmarks that have been added on the patient's face. The camera may be positioned on the apparatus 10, e.g. on the arm 22 or independent from the apparatus. On FIG. 1 an example of a camera 52 is located next to x-ray source 18. Another location for a camera may alternatively or in addition be selected.

Alternatively, a lateral optical image of the patient may be convenient instead of the facial one.

The landmark or landmarks are representative of a geometrical position that is known or can be easily known by computation relative to the teeth roots.

As a consequence, the height of a horizontal plane (ex: median plane) of ROI1 that can be used for the first x-ray data acquisition can therefore be determined by computation based on the position of the landmark or landmarks (step S2.2).

A third way (step S2.4) makes provision for performing physical measurements on the patient (in a biting position or in the occlusal position), more particularly on the patient's maxillofacial first region of interest (ROI1), using a patient positioning device or accessory.

A patient positioning accessory attached to the arm 22 of FIG. 1 may be used, e.g. a bite block or the like. The bite block is attached to the arm in a fixed position and the height of the bite block relative to the arm is known or can be measured. The mean size (height) of teeth for a given patient (adult, child etc.) are also known, which makes it possible to situate the position of teeth roots and therefore their position relative to the teeth extremities, i.e. the bite block.

Consequently, the height or position of the horizontal plane of ROI1 relative to the arm may be determined by measurements and/or computation based on the above.

Alternatively, a sensor located in the bite block or the like may provide appropriate measurement data and the height or position of the occlusal plane relative to the arm may next be determined therefrom.

Then, the height of a horizontal plane of ROI1 that can be used for the first x-ray data acquisition can be determined based on the position of the occlusal plane (step S2.2). This prior determination phase aims at determining the height at which the first set of data relating to ROI1 will be acquired.

Figure 3:
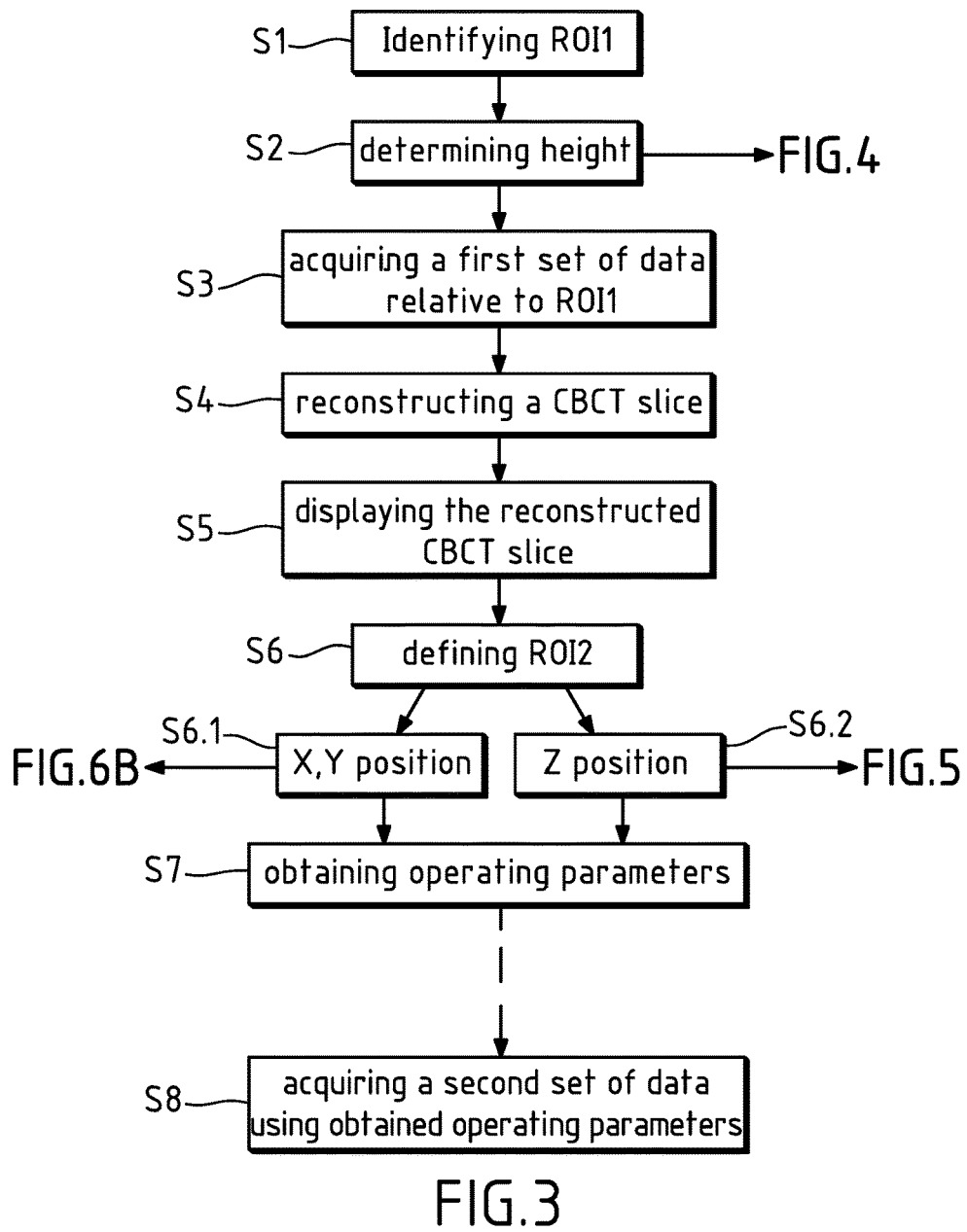
FIG. 3 shows an algorithm of a method according to an embodiment of the invention.

Once the height of the horizontal plane has been determined, the apparatus 10 is set by control assembly 44 in a configuration that enables acquisition of the first set of data relative to ROI1 as provided by step S3 of FIG. 3. The first set of data may correspond to the whole ROI1 or to a selected portion thereof.

Two ways are used for setting the apparatus in the acquisition configuration/
firstly, the set of x-ray source and x-ray sensor is commanded by control assembly 44 to be moved to the determined height so that the x-ray source be at the appropriate height for the acquisition; this arrangement makes it possible to reduce the x-ray dose easily;

secondly, the x-ray source remains at the same altitude and the x-ray collimator is moved so as to orientate the x-ray beam upwardly towards the determined height of the plane.

For this first data acquisition the patient remains in the biting position (or occlusal position) as provided for at previous step S2. The patient may also be positioned so that his/her Camper plane be horizontal as for step S2.

The patient is placed in an appropriate position (first position) for this first data acquisition, e.g. using a patient positioning device or accessory of the apparatus (here a bite block) and possibly a seat.

The different setting parameters that define the first position of the patient, such as the accessory used, the position of this accessory on the apparatus if several position settings are available (ex: different possible heights for a support) and the accessory position relative to the patient (ex: if several width values are possible in accordance with the patient's face width), the height of the possible seat if this parameter is adjustable, etc. are recorded or stored by the practitioner (ex: in a storage medium through the user interface assembly) with a view to being used again for a subsequent data acquisition.

For this first data acquisition the apparatus 10 is in an operating CBCT mode under the control of control assembly 44.

According to this mode the x-ray collimator opening is adjusted as a slit-shaped collimator window so as to produce a slit shaped x-ray beam focused on the patient's maxillofacial first region of interest (ROI1) including the horizontal plane.

This slit shape for the beam is adjusted so as to cover the ROI1 and preferably a thin volume in height.

The horizontal plane of ROI1 is aimed at thanks to the adjustment in the collimator position and the collimator window opening.

Figure 6A:
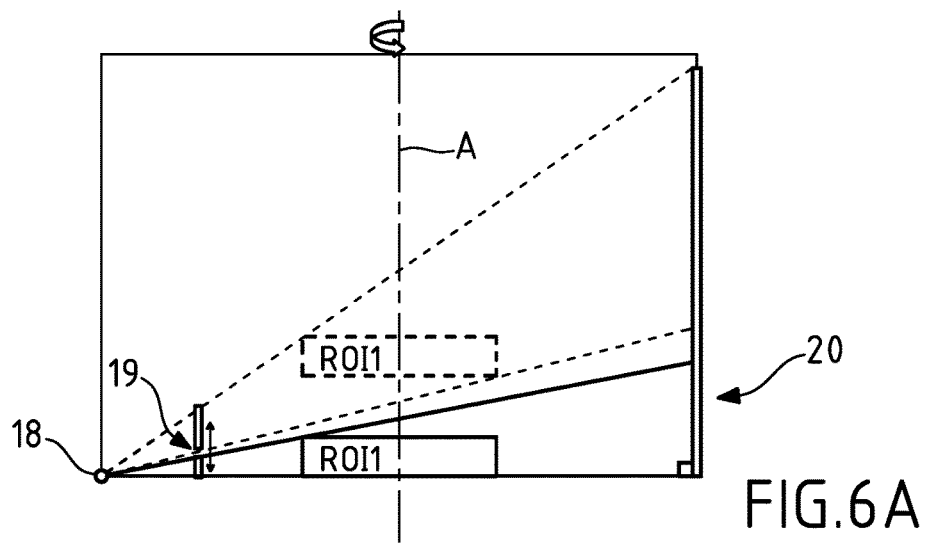
FIG. 6A illustrates possible relative positions between the ROI1 and the x-ray source.

FIG. 6A illustrates two different relative positions between the x-ray source 18 and ROI1 (ROI1 could alternatively be replaced by a portion thereof and the remainder of the description applies equally) with different openings for the x-ray collimator 19. As represented, the x-ray source 18 is in alignment with the lower end of the sensor 20.

The axis of rotation A of the set composed of the source and the sensor has also been illustrated. In order to capture and reconstruct a CBCT slice, the opening of the collimator in the vertical direction depends on the position of the collimator relative to the source-sensor alignment. The smallest opening is obtained when the source-sensor axis passes by the collimator. In other words, the median plane of the collimated x-ray beam may be adjusted so as to obtain for the collimator the smallest opening that is necessary for the slice reconstruction.

Preferentially, the source-sensor axis passes by the basis of the collimator window and the lower edge or boundary of ROI1.

The x-ray source is operated with a first x-ray dose that may be qualified as a low dose with respect to the x-ray dose that will be used for a subsequent second data acquisition.

The first x-ray dose is selected so as to minimize x-ray exposure for the patient. The x-ray dose depends on the volume of patient data to be acquired. The volume is preferably as small as possible and does not need high resolution for data acquisition since the useful information that is needed for the remainder of the method lies in the morphological characteristics or data of the patient maxillofacial first region of interest (location of the teeth, characteristic dimensions, etc.). Preferably, such information does not require many details in the acquired data. However, the volume is not necessarily thin and its size depends on the resolution of the image. A compromise between the size and resolution of the volume has generally to be made if the dose is to be low.

Typically, the first x-ray dose does not exceed 20% of the second dose that will be used for a subsequent second data acquisition.

Preferentially, the first x-ray dose does not exceed 10% of the second dose and, more preferentially, does not exceed 5% of the second dose.

For example, a first x-ray dose may be in the order of 4 uSv for generating a CBCT slice.

The information that is needed in the data volume to be acquired during this first acquisition (CBCT slice) will be used for appropriately positioning the data volume to be acquired during a subsequent second acquisition.

Reverting to FIG. 3, the third step S3 for acquiring a first set of data (3D volume) is based on the above settings and adjustments. This first acquisition may be viewed as a "pre-shoot" for providing useful information that will be used for a "shoot". The exposure time for this pre-shoot may be rather low, e.g. in the order of 5 s.

Next step S4 is a reconstruction step for reconstructing a CBCT slice based on the acquired first set of data using conventional CBCT data processing techniques (e.g. the FDK algorithm).

The reconstructed CBCT slice comprises the horizontal plane of ROI1 and is based on the acquired first set of data relative to the patient's maxillofacial first region of interest (ROI1).

As an example of a low resolution in the first acquired data a voxel size around 500 μm in the reconstructed CBCT slice can be obtained. For example, the thickness or height of the slice lies between 10 and 30 voxels, thereby corresponding to a range between 1 and 15 mm. Preferentially, a range between 1 and 5 mm may be selected.

The reconstructed CBCT slice may take the shape of a cylinder (another shape may be used) with a diameter lying between 120 mm (for small skull dimensions) and 160 mm Smaller diameters may be convenient. The CBCT slice may be qualified here as a thin slice. In other example embodiments acquisition of the whole dental arch may be aimed at.

Figure 6B:
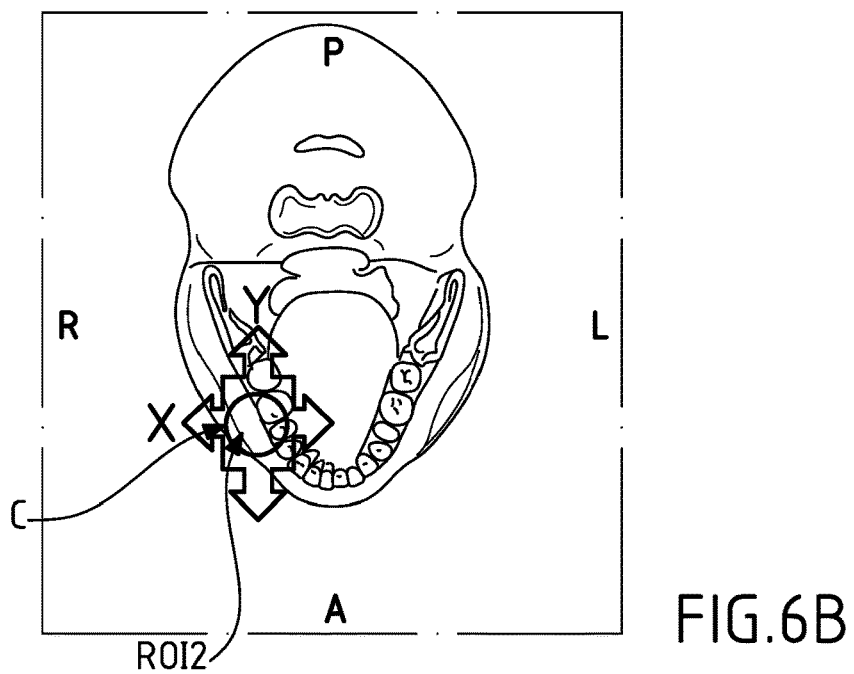
FIG. 6B shows an axial view of the reconstructed CBCT slice with the ROI2.

The method further comprises a display step S5 for displaying on display assembly 48 of FIG. 2 an axial slice of the reconstructed 3D volume (CBCT slice of the patient's maxillofacial first region of interest ROI1) as illustrated on FIG. 6B (horizontal plane). Additional views may also be displayed where necessary, e.g. a sagittal view.

The method further comprises a step S6 for defining at least partially a second region of interest ROI2 based on the reconstructed and displayed axial CBCT slice of the patient's maxillofacial first region of interest ROI1. The second region of interest ROI2 is defined or selected so as to intersect the first region of interest ROI1 in the x, y plane of the axial slice.

The second region of interest ROI2 is defined or selected by the practitioner through user interface assembly or Graphical User Interface 50. For instance, the practitioner selects, through activating a user input tool such as clicking on a mouse, the display of a menu or set of icons and further selects an icon that can be moved to the desired position on the displayed slice thanks to the movement of the mouse cursor. The icon is represented here by a circle C on FIG. 6B since in this embodiment the second volume of data to be subsequently acquired is a cylinder. The circle appearing on the view has the dimensions of the second volume of data to be acquired.

In addition, the second volume of data to be subsequently acquired may take another shape and the landmark or icon that helps defining the ROI2 may take another shape in register therewith.

Reverting to FIG. 6B, the position and the size of the circle on the displayed axial slice define the second region of interest ROI2 that intersects the first region of interest ROI1 in the x, y plane of this Figure.

On FIG. 6B, the circle (ROI2) has been positioned in part on a group of teeth.

As illustrated, the position of the ROI2 can be adjusted according to x and y coordinates in the plane of FIG. 6B (see the corresponding left, right, up and down arrows) so as to define the desired position in accordance with the practitioner needs (step S6.1). In particular, he/she may need to focus on one tooth or a group of teeth for the next and more accurate data acquisition.

To be noted that the size of the circle (here its diameter) may be adjusted where necessary to enlarge or reduce the size of the second region of interest ROI2 to be defined. The size may be varied e.g. by scrolling the mouse wheel for example. The size of the circle may be changed by selecting a value among a set of predetermined values.

The above-described size and/or position adjustments of ROI2 may be viewed on display in real time by the practitioner, which makes it possible to further adjust the size and/or position where necessary.

All that has been described above in connection with a circle and a mouse equally applies to other displayed landmarks and user input tools, as well as the operation of both landmarks and user input tools to define the second region of interest.

In step S6.2 the position of the ROI2 can also be defined or adjusted according to an axis z that is perpendicular to the x, y plane of FIG. 6B so as to finish defining the desired position of the second volume of data in accordance with the practitioner needs.

The z-axis position or height of ROI2 (Field Of View or FOV) may be defined or adjusted based on a lateral scout view. The lateral scout view may advantageously be that used for determining the height of the horizontal plane of interest at step S2 above and illustrated on FIG. 5 (LSV).

The lateral scout view LSV provides the practitioner with additional morphological information such as indication about the location of teeth and their geometries in a vertical plane (y, z plane). This may help the practitioner to further define the position of the ROI2 relative to the maxillofacial region, in particular as regards the z-axis position. In addition, the y-axis position of the ROI2 may also be better defined or adjusted thanks to lateral scout view LSV.

The height or size in height of ROI2 may have a predetermined value and may be changed upon command by the practitioner so as to increase or reduce the second volume of data to be acquired. The same process as that described above for the size (e.g. diameter for a circle) of the circle C may also apply here for modifying the z-axis position. To be noted that the practitioner may flip back and forth between the views of FIGS. 5 and 6B to manually adjust x, y and/or z-axis positions of ROI2 and/or size thereof.

The height or size in height of the ROI2 may be changed by selecting a value among a set of predetermined values.

In the present embodiment, as already mentioned above the second volume of data to be acquired may take the shape of a cylinder whose dimensions may vary according to the practitioner's needs.

To be noted that defining the geometric position of the ROI2 sets the position of the center of the ROI2.

It has been explained above how to define or adjust the z-axis position or height of ROI2 based on a lateral scout view.

However, more generally, the z-axis position or height of ROI2 may be defined or adjusted based on determining the height of the horizontal plane of interest as described at step S2 above. In particular, other processes than the lateral scout view may be used such as acquiring an optical image or performing physical measurements as described above at steps S2.3 and S2.4.

Alternatively, the z-axis position or height of ROI2 may be defined or adjusted independently from the determination of the height of the plane of interest as described at step S2 above. The z-axis position or height of ROI2 may then be defined or adjusted based on one of the following that is performed on purpose for achieving this goal:

acquiring a lateral x-ray scout view comprising the patient's maxillofacial first region of interest (ROI1);

acquiring an optical image comprising the patient's maxillofacial first region of interest (ROI1) including landmarks;

performing physical measurements on the patient's maxillofacial first region of interest (ROI1) using a patient positioning device.

The above steps are identical to those described above in connection with steps S2.1, S2.2, S2.3 and S2.4. However, in this alternative embodiment method the same step may be performed twice, one for determining the height of the plane of interest and the other for defining the z-axis position of the ROI2.

As a variant embodiment, the step for defining or adjusting the z-axis position of ROI2 may be different from that performed at step S2. For example, a lateral scout view is acquired to be used for defining or adjusting the z-axis position of ROI2 whereas step S2 has been carried without using a lateral scout view.

It is to be noted that the size in height of the ROI2 may extend beyond the height of the CBCT slice which is here rather thin, e.g. in the order of 1-15 mm, preferably, 1-5 mm.

The method further comprises a step S7 for obtaining operating parameters based on at least the thus defined ROI2.

As seen above the ROI2 has been defined by its x, y and z spatial coordinates which set the spatial or geometric position of the center of the ROI2 and size. This position and size information on the ROI2 has thus been obtained with accuracy based on patient's data and not on averaged patient's data. This therefore makes it possible for the practitioner to adjust the trajectory of both the x-ray source and x sensor to subsequently acquire a 3D volume (second set of data including the ROI2) based on the ROI2 position and size. To be noted that the trajectory may be based on the ROI2 position only. Both the x-ray source and x sensor will be operable to simultaneously move around the patient's head along this trajectory. Preferably, the 3D volume corresponds to the volume of data of the ROI2. However, other configurations may be envisaged.

Through this adjustment the position of the center of rotation of the set of the x-ray source and x sensor may be modified in accordance with the targeted anatomy (ex: ROI2).

Figure 7:
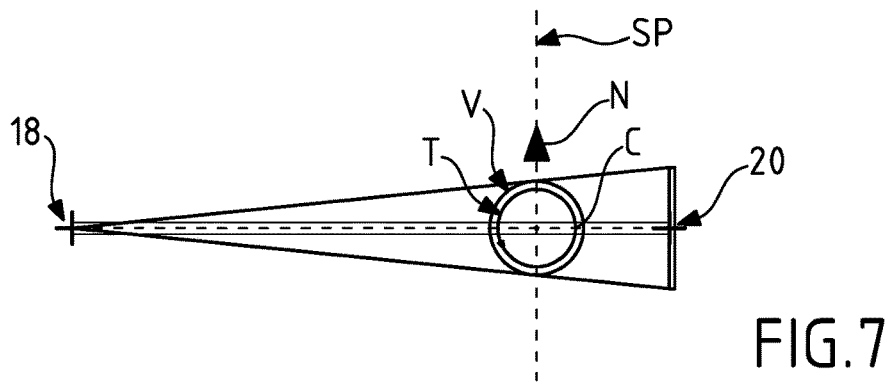
FIG. 7 shows an example of a trajectory for both an x-ray source and an x-ray sensor.

An example of a possible trajectory for both x-ray source 18 and x sensor 20 is illustrated on FIG. 7 on which the following notations have been used:

C: center of rotation of the gantry;
N: nose of the patient;
SP: sagittal plane of the patient;
T: trajectory followed by the center C;
V: 3D volume that is reconstructed/obtained through describing trajectory T.

In a general manner, the position and size of the ROI2 are operating parameters as well as the shape of the ROI2 which is here a cylinder in the example embodiment.

If the 3D volume to be subsequently acquired does not correspond to the ROI2, the operating parameters to be used during this subsequent acquisition may differ from the above.

The obtained operating parameters make it possible to determine a plurality of trajectories which each make it possible to obtain the desired 3D volume.

The obtained operating or acquisition parameters of step S7 can then be stored while waiting for being used.

All the operating parameters are obtained based on the defined ROI2 which accurately represents the region of interest for the practitioner without any unnecessary details (optimization of the position of the ROI or 3D volume to be subsequently acquired).

Therefore the obtained operating parameters are tailored to the specific needs of the practitioner and reduce as much as possible the patient's area that will be exposed to x-rays as well as the x-ray dose to be used.

To be noted that a few steps (other than manual steps S1 and S6) may be performed automatically by control assembly 44 of FIG. 2 in the embodiment method of FIG. 3.

The operating or acquisition parameters that have been obtained at step S7 may be used in the course of a subsequent step S8 for acquiring a second set of data relating to the patient's maxillofacial second region of interest (ROI2) and including the latter using a second x-ray dose. This second set of data to be acquired corresponds to the above 3D volume of data.

This acquisition step will be performed with an x-ray CBCT imaging apparatus that is not necessarily the apparatus 10. This acquisition step may be separate in time from the first steps S1 to S7, e.g. by several hours, days, months, etc. It will be assumed that the patient's maxillofacial region has not changed between the two acquisitions.

Here the method step S8 comprises a prior patient positioning step before acquiring a second set of data, using the recorded or stored different setting parameters defining the first position of the patient (see above steps S2 and S3). This prior step makes provision for adjusting the setting parameters in the x-ray CBCT imaging apparatus, in particular of the patient positioning device or accessory used at step S3, so that the patient be positioned in the same first position or close to in view of this second data acquisition.

The obtained operating or acquisition parameters (ex: trajectory, x-ray dose, etc.) are next used at step S8 to adjust or set the x-ray CBCT imaging apparatus in view of acquiring a 3D volume of data including the ROI2 relative to the patient's maxillofacial region.

The x-ray dose that is used for this second data acquisition is higher than the first x-ray dose for generating a slice: the first x-ray dose is less than or equal to 20% of the second x-ray dose, preferably less than or equal to 10% and more preferably less than or equal to 5%.

By way of example, the first x-ray dose is 4 μSv and the second x-ray dose is:

200 μSv for a 3D examination with a large field of view (17×13 cm);
20 μSv for a 3D examination with a 5×5 cm field of view.

By way of example, the duration of the exposure to x-ray for the second data acquisition is between 5 and 20 s for a 3D examination compared with an approximately 5 s duration for the first data acquisition.

By way of example, the resolution of the image(s) obtained through the second data acquisition is defined by a 100 μm voxel size for a 3D examination compared with a 500 μm voxel size for the first data acquisition.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for obtaining operating parameters for an x-ray CBCT imaging apparatus in view of acquiring a set of data of a patient's maxillofacial region, the method comprising the steps of:

identifying a patient's maxillofacial first region of interest (ROI1);

determining a height of a horizontal plane of said patient's maxillofacial first region of interest (ROI1) when the patient is in an occlusion position or bites a patient positioning accessory;

acquiring through a slit-shaped collimator window a first set of data relative to said patient's maxillofacial first region of interest (ROI1) including the horizontal plane using x-ray CBCT imaging, wherein the acquired first set of data comprises a first set of x-ray images obtained at different angular positions relative to the patient's maxillofacial first region of interest (ROI1);

reconstructing an axial CBCT slice comprising the horizontal plane based on the first set of data relative to the patient's maxillofacial first region of interest (ROI1);

displaying the reconstructed axial CBCT slice of the patient's maxillofacial first region of interest (ROI1) from the acquired first set of data;

defining at least partially a second region of interest (ROI2) based on the displayed reconstructed axial CBCT slice of the patient's maxillofacial first region of interest (ROI1) and intersecting the reconstructed axial CBCT slice of the patient's maxillofacial first region of interest (ROI1); and obtaining operating parameters for an x-ray CBCT imaging apparatus based on at least the defined second region of interest (ROI2) in view of acquiring a second set of data including the defined second region of interest (ROI2).

2. The method of claim 1, wherein defining at least partially the second region of interest (ROI2) based on the displayed reconstructed axial CBCT slice of the patient's maxillofacial first region of interest (ROI1) includes defining the position of the second region of interest (ROI2) in the x, y plane of the axial CBCT slice.

3. The method of claim 2, wherein defining the second region of interest (ROI2) further includes defining the position of the second region of interest (ROI2) along a z-axis (height) that is perpendicular to the x, y plane of the axial CBCT slice.

4. The method of claim 3, wherein defining the z-axis position of the second region of interest (ROI2) includes beforehand one of the following steps:
  acquiring a lateral x-ray scout view comprising the patient's maxillofacial first region of interest (ROI1); or
  acquiring an optical image comprising the patient's maxillofacial first region of interest (ROI1) including landmarks; or
  performing physical measurements on the patient's maxillofacial first region of interest (ROI1) using a patient positioning device.

5. The method of claim 4, wherein the method further comprises a step of adjusting the height of the second region of interest (ROI2) based on the lateral scout view, the optical image, or the performed physical measurements.

6. The method of claim 3, wherein the z-axis position of the second region of interest (ROI2) is predetermined.

7. The method of claim 1, wherein the second region of interest (ROI2) has a size that is selected from a set of predetermined values.

8. The method of claim 3, wherein defining the z-axis position of the second region of interest (ROI2) is based on determining the height of a horizontal plane of said patient's maxillofacial first region of interest (ROI1) when the patient is in an occlusion position or bites a patient positioning accessory.

9. The method of claim 1, wherein determining the height of the horizontal plane of said patient's maxillofacial first region of interest (ROI1) when the patient is in an occlusion position or bites a patient positioning accessory includes beforehand one of the following steps:
  acquiring a lateral x-ray scout view comprising the patient's maxillofacial first region of interest (ROI1); or
  acquiring an optical image comprising the patient's maxillofacial first region of interest (ROI1) including landmarks; or
  performing physical measurements on the patient's maxillofacial first region of interest (ROI1) using a patient positioning device.

10. The method of claim 1, wherein the first set of data is acquired while the patient is maintained in a first position through a patient positioning device, said first patient position being defined by a set of setting parameters for the patient positioning device.

11. The method of claim 10, wherein the method further comprises prior adjusting of the setting parameters of the patient positioning device before acquiring the second set of data.

12. The method of claim 1, wherein the first set of data and the second set of data are separate in time.

13. The method of claim 1, wherein the x-ray CBCT imaging apparatus comprises an x-ray source and an x-ray sensor that are both operable to simultaneously move around the patient's head along a predetermined trajectory, and wherein obtaining operating parameters for the x-ray CBCT imaging apparatus based on the defined second region of interest (ROI2) comprises adjusting a trajectory for both the x-ray source and the x-ray sensor based on the defined second region of interest ROI2.

14. A computer storage medium having instructions stored therein for causing a computer or a microprocessor to perform the method of claim 1.

15. The method of claim 1, further comprising the steps of:
  acquiring the second set of data that comprises a second set of x-ray images obtained at different angular positions including the defined second region of interest (ROI2); and
  reconstructing a 3D CBCT image including the defined second region of interest (ROI2); based on the second set of data relative to the patient's maxillofacial second region of interest (ROI2).

16. The method of claim 15, wherein the 3D CBCT image has a higher resolution than the axial CBCT slice.

17. A system for obtaining operating parameters for x-ray CBCT imaging a patient's maxillofacial region, comprising:
  an x-ray source and at least one x-ray sensor that are configured to move around a patient's maxillofacial first region of interest (ROI1) while irradiating the latter with a slit-shaped x-ray beam so as to acquire a first set of data relative to said patient's maxillofacial first region of interest (ROI1) when the patient is in an occlusion position or bites a patient positioning accessory, said patient's maxillofacial first region of interest (ROI1) including a horizontal plane, wherein the acquired first set of data comprises a first set of x-ray images including the horizontal plane obtained at different angular positions relative to the patient's maxillofacial first region of interest (ROI1); and
  a microprocessor configured to:
    reconstruct an axial CBCT slice comprising the horizontal plane based on the first set of data relative to the patient's maxillofacial first region of interest (ROI1),
    display the reconstructed axial CBCT slice of the patient's maxillofacial first region of interest (ROI1) from the acquired first set of data with a view to defining at least partially a second region of interest (ROI2) that is based on the displayed reconstructed axial CBCT slice and intersects the latter, and
    obtain operating parameters for an x-ray CBCT imaging apparatus based on at least the defined second region of interest (ROI2) in view of acquiring a second set of data including the defined second region of interest (ROI2).

18. The system of claim 17, wherein the obtained operating parameters for the x-ray CBCT imaging apparatus based on the defined second region of interest (ROI2) comprise an adjusted trajectory for both the x-ray source and the x-ray sensor based on the defined second region of interest ROI2.

* * * * *